United States Patent [19]

Hamlin et al.

[11] Patent Number: 5,786,491
[45] Date of Patent: Jul. 28, 1998

[54] PROCESS FOR CRYSTALLIZING D-ALPHA-TOCOPHERYL SUCCINATE

[75] Inventors: Michael David Hamlin, Brockport, N.Y.; Richard Wayne Connelly, Rochester, N.Y.

[73] Assignee: Eastman Chemical Company, Kingsport, Tenn.

[21] Appl. No.: 761,276

[22] Filed: Dec. 6, 1996

[51] Int. Cl.[6] .................................................. C07D 311/04
[52] U.S. Cl. ............................................................ 549/407
[58] Field of Search ............................................. 549/407

[56] References Cited

U.S. PATENT DOCUMENTS 4,683,326  7/1987  Orban et al. .
5,686,632  11/1997  Walsh .

OTHER PUBLICATIONS

"Disruptive Processes in the Shear Crystallization of Poly-(Ethylene Oxide)", Polymer Engineering and Science, Mar., 1976, vol. 16, No. 3, pp. 182–186.

Primary Examiner—Johann Richter
Assistant Examiner—Taofiq A. Solola
Attorney, Agent, or Firm—Charles R. Martin; Harry J. Gwinnell

[57] ABSTRACT

Disclosed is a process for whereby d-alpha-tocopheryl succinate (TS) can be crystallized in a short period of time by subjecting a fluid TS at particular temperature to a particular rate of shear for a particular time in order to accomplish crystallization. Then, while maintaining the crystallized TS at a temperature less than its melting point, we withdraw the crystallized TS from the region of shear flow. In a preferred embodiment of our process, crystallization is enhanced by use of a particular elongational rate for a particular time.

6 Claims, No Drawings

PROCESS FOR CRYSTALLIZING D-ALPHA-TOCOPHERYL SUCCINATE

This invention relates to the use of shear to crystallize d-alpha-tocopheryl succinate.

D-alpha-tocopheryl succinate, often abbreviated herein as TS, is a well known compound which is a form of vitamin E and is prepared commercially by esterifying liquid vitamin E derived from natural sources with succinic anhydride. TS has a number of uses, including use as a nutritional supplement.

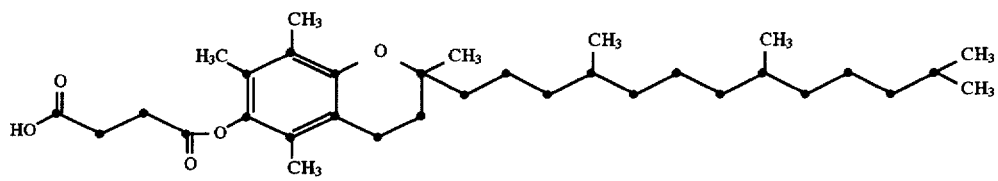

When TS is used as a nutritional supplement, it is necessary that the TS be converted from a liquid to a solid so that it can be ground by conventional means in preparation for tableting. In order to accomplish this change, the molten TS must be crystallized.

TS can be crystallized according to well known techniques; however, these techniques are frequently batch crystallization processes requiring long periods of time, such as twenty hours or more to form the desired crystalline solid.

We have now invented a continuous process whereby TS can be crystallized in a very short period of time. For example, according to the process of this invention TS can normally be crystallized in less than 20 minutes and is some cases less than 5 minutes.

In accordance with the process of this invention, we subject a fluid TS at a particular temperature to a particular shear rate for a particular time in order to accomplish crystallization. Then, while maintaining the crystallized TS at a temperature less than its melting point, we withdraw the crystallized TS from the region where the shear flow was induced. In a preferred embodiment of our process, crystallization is enhanced by use of a particular elongation rate for a particular time.

The broadest embodiment of the process of this invention can be thought of as composed of three steps.

First, fluid TS is introduced into a crystallization zone at a temperature in the range of about 0° to about 200° C.

Second, the TS is subjected to a shear rate of at least 1/s. for at least 5 seconds within the crystallization zone, while heat is removed by cooling.

Finally, the TS is withdrawn from the crystallization zone at a temperature less than the melting point of the TS.

In the preferred embodiment, crystallization is enhanced in the second step by use of an elongational rate of at least 1/s. for at least 5 seconds.

The compound which can be crystallized in accordance with the process of this invention is the succinic acid ester of natural source vitamin E, or d-alpha-tocopheryl succinate (TS). This compound corresponds to the following structure wherein the methyl group bonded to the same carbon atom to which the side chain is bonded is oriented toward the viewer from the plane in which the heterocyclic ring resides, the side chain is oriented away from the viewer and away from the plane in which the heterocyclic ring resides, both methyl groups on the side chain are oriented away from the viewer and away from the plane in which the side chain resides and the corresponding hydrogen atoms bonded to the same carbon atom on the side chain are oriented toward the viewer from the plane in which the side chain resides. This compound is also referred to as (2R, 4'R, 8'R)-alpha-tocopheryl succinate.

In this invention we use the term crystallization, and words of similar import, in its ordinary sense and means the phenomenon of crystalline formation.

In accordance with this invention, the d-alpha-tocopheryl succinate can be crystallized in the presence of minor amounts of other materials which do not interfere with practice of the invention. Therefore, by the term d-alpha-tocopheryl succinate, and the abbreviation TS, we mean the above described compound as well as mixtures of d-alpha-tocopheryl succinate which do not contain more than 10 weight percent, based on the weight of the d-alpha-tocopheryl succinate, of other materials which are suitable for use in the process of this invention. These materials typically exist because they were involved in a prior processing step or were present in the vitamin E oil (tocopherol) raw material and it is not economically attractive to entirely remove the materials from the TS. The specific materials will depend on the particular process used to prepare the TS but typically can be thought of as trace amounts of residual crystallization solvents, wash reagents, or succinic acid or anhydride, tocopherols, and the like.

In this invention, the TS is crystallized from a fluid state. The term "fluid" is used in its ordinary meaning and means that the TS changes shape or direction uniformly in response to an external force.

An important aspect of this invention is the temperature of the TS when it enters the region of shear flow. The temperature of the TS must be within the range of about 0° to about 200° C., preferably within the range of about 75° to about 100° C. and most preferably within the range of 80° to 90° C. It is important the TS not be at a temperature of less that about 0° C. because TS will exist as an amorphous solid material at low temperatures preventing it from being handled and inhibiting crystal formation. It is also important the TS not be at a temperature greater than about 200° C. because the TS cannot be crystallized until it is cooled below its melting point of 75° C. Temperatures in the range of about 75° to about 100° are more preferred because the material can be pumped more easily. Temperatures in the range of 80° to 90° C. are most preferred because temperatures in this range minimize the possibility the TS will crystallize in the process feed system but are cool enough that sensible heat required for removal is reduced, thus improving the capacity of the crystallization equipment.

In this invention the TS is subjected to nonhomogeneous unsteady shear flows and shearfree flows or combinations thereof. The shear flows are characterized by a nominal shear rate equal to the relative sliding velocity of two shearing planes divided by the distance between them. The shearfree flows are characterized by an elongation rate equal to the relative velocity of two points along the flow axis per unit of distance.

Another important aspect of this invention is the rate at which shear is applied to the TS and the period of time the shear rate is applied. Broadly, the shear can be applied at a rate of at least 1/s. for at least 5 seconds. More preferably the shear rate is in the range of 10 to 1000/s. and the time is at least 10 seconds. Most preferably, the shear rate is in the range of 100 to 600/s. for at least 20 seconds. During this step, the rate of shear must be at least 1/s. for at least 5 seconds to affect crystallization. Preferably a shear rate of 10 to 1000/s. is used for at least 10 seconds to affect crystallization. Most preferably, the shear rate should be in the range of 100 to 600/s. for at least 20 seconds. A shear rate in excess of 500/s. results in additional energy input which creates heat and results in lower process capacity due to an increased cooling requirement.

In the optional preferred embodiment wherein elongational flow is used in addition to shear flow, the elongational flow rate is at least 1/s. for at least 5 seconds, preferably is in the range of 1 to 1000/s. for at least 20 seconds and most preferably is in the range of 100 to 600/s. for at least 5 minutes.

The TS can be crystallized using any apparatus which will remove sensible heat, heat of crystallization and heat generated as a result of mechanically working the TS, and which will create the required shear rate for the required time and, optionally, also the required elongation rate for the required time. A particularly preferred apparatus is manufactured by Teledyne Readco, York, Pa. and is sold under the name "Teledyne Readco Continuous Processor". This equipment comprises a housing which has an inlet and outlet and forms a passageway having a cross section corresponding to two equal diameter circles having their centers spaced apart about three-fourths of the diameter of the circle. A shaft is positioned at the center of each of the circles and extends along the length of the passageway. Each shaft is driven by suitable means to cause the shafts to rotate in the same direction. Each shaft is adapted to retain a plurality of somewhat elliptically shaped paddles having a larger diameter approaching the diameter of the circle. The thickness and diameter of the paddles can vary depending on the size and model of continuous processor used to practice this process. The thickness of the paddles create a face which contacts the TS during the application of shear flow and elongational flow. The flat sides also apply shear flow to the TS. The thickness, smaller diameter and larger diameter of the elliptical paddles are composed to provide the required shear rate when the paddles are caused to rotate in the same direction by the movement of the shafts.

In operation, a fluid TS to be crystallized is introduced into the inlet within the correct temperature range. The number of elliptical paddles as well as the thickness, smaller diameter, larger diameter and slant of the paddles can be readily selected by those skilled in the art to create the required rate of shear, cause the TS to remain in the region of shear flow for the required time and create any elongational flow required. The time the TS is within the region of shear flow can be further controlled by increasing or decreasing the rate at which the fluid TS is introduced into the inlet of the machine.

Although the above described equipment is preferred for creating the required shear rate for the required time, other apparatus can be used and the particular apparatus which is selected to create the required shear rate for the required time is not a critical aspect of the invention. For example, the invention may be practiced using batch mixing, spray atomization, spinning disc atomization or scraped surface heat exchange equipment.

After the TS has been subjected to the required shear rate for the required time, and optionally also elongational flow, the TS is withdrawn from the apparatus at a temperature less than the melting point of the TS. It is essential that the temperature of the TS be less than the melting point of the TS because crystallization will not occur above the melting point.

As will be recognized by those skilled in the art, subjecting the TS to shear flow creates heat due to mechanical manipulation of the TS and the exothermic nature of the crystallization phenomenon. As a result of this generation of heat and the need to insure that the TS is at a temperature less than its melting point when it exits the region of shear flow, heat must be removed from the process. The temperature at which the crystallized TS leaves the region of shear flow can be readily controlled by those skilled in the art by controlling the residence time of the TS, by adjusting the feed rate, in the equipment and by controlling the temperature of jacket cooling fluid. The residence time of the TS within the region of shear flow can be controlled as previously described. The walls of the equipment are cooled by use of a jacket surrounding the passageway wherein water or other suitable heat transfer fluid is circulated.

If desired, the crystallization rate can be enhanced, often significantly, by "seeding" the molten TS with crystalline TS powder. Although it is only a hypothesis, we believe the presence of entrained air also facilitates the formation of TS crystals. Provisions for seeding are more significant in a batch processing application of this invention since the continuous processor application of this invention provides seeding by continuously blending fresh, uncrystallized TS feed with partially crystallized TS already in the mixing chamber. The application of seeding was tested using a high intensity batch mixer with counter-rotating screws. It was found that seeding provided significant reduction (better than 60%) in mixing time required to crystallize TS when the mixing chamber and screws were not cleaned between experimental runs to remove all traces of TS.

In accordance with this invention, the TS which exits the process has a physical form similar to a dough used to prepare bakery products; however, the TS dough is not sticky. The TS dough is at a temperature less than the melting point of TS and is partially crystalline as a result of practicing the process of this invention. Upon standing, the TS dough continues to crystallize and is solid within 30 minutes.

Depending entirely on the manner in which the TS is to be used, the solid TS which results from practicing this invention can be ground using techniques well known in the art. The TS can be ground into a powder, a mixture of powder and chips, or larger size particles.

The process of this invention has many advantages compared to prior processes but one of the most important advantages is that practice of this process results in a very clean production environment. The clean production environment results from the process being continuous and the TS being entirely confined within piping and equipment during the entire process.

The following illustrates a preferred embodiment of the practice of our invention.

The Teledyne Readco Continuous Processor described previously was selected to create the required shear flow and elongational flow.

The 5 inch paddle size Processor has an internal volume of 0.501 cubic feet, a maximum torque input of 20 horsepower at 100 rpm and was equipped with a cooling jacket.

The Processor was cleaned with soap and purged with nitrogen. Ninety lb/hr of fluid TS at a temperature of about 85° C. was fed to the Processor. At this throughput, calculations revealed that the Processor was drawing 3.0 hp with a mechanical loss of 0.8 hp. An amount of shear energy equivalent to 62 BTU/lb was calculated as being delivered to the TS. The heat transfer coefficient was calculated to be 18 BTU/hr–ft$^2$–°F. The maximum shear rate at the paddle tips was calculated to be 520/s. and the elongational rate was estimated to be between 260/s and 520/s. The TS was subjected to this shear rate and elongational rate for a residence time of about 5 minutes.

The feed rate and cooling rate were adjusted so that the temperature of the crystallized TS exiting the Processor was about 40° C.

A sample of the crystallized TS was crumbled without difficulty. The crumbled sample was satisfactorily ground at room temperature using a laboratory blender. It was observed the energy requirement for grinding was significantly less than the energy requirement for grinding an TS which had been crystallized in accordance with another process.

The ability of the TS produced by the process described in this invention to prepare tablets was compared to the ability of TS produced using prior technology to prepare tablets. The TS prepared using the process of this invention had a similar ability to be prepared into tablets compared to the TS prepared using prior technology.

We claim:

1. A process comprising
   (A) introducing an d-alpha-tocopheryl succinate in a fluid state into a crystallization zone at a temperature in the range of about 0° to about 200° C.,
   (B) subjecting the d-alpha-tocopheryl succinate to a shear rate of at least 1/second for at least 5 seconds within the crystallization zone, and
   (C) withdrawing the d-alpha-tocopheryl succinate from the crystallization zone at a temperature less than the melting point of the d-alpha-tocopheryl succinate.

2. A process comprising
   (A) introducing an d-alpha-tocopheryl succinate in a fluid state into a crystallization zone at a temperature in the range of about 75° to 100° C.,
   (B) subjecting the d-alpha-tocopheryl succinate to a shear rate in the range of 10 to 1000/second for at least 10 seconds within the crystallization zone, and
   (C) withdrawing the d-alpha-tocopheryl succinate from the crystallization zone at a temperature in the range of 23° to 55° C.

3. A process comprising
   (A) introducing an d-alpha-tocopheryl succinate in a fluid state into a crystallization zone at a temperature in the range of 80° to 90° C.,
   (B) subjecting the d-alpha-tocopheryl succinate to a shear rate in the range of 100 to 600/second for at least 20 seconds within the crystallization zone, and
   (C) withdrawing the d-alpha-tocopheryl succinate from the crystallization zone at a temperature in the range of 35° to 45° C.

4. A process comprising
   (A) introducing an d-alpha-tocopheryl succinate in a fluid state into a crystallization zone at a temperature in the range of about 0° to about 200° C.,
   (B) subjecting the d-alpha-tocopheryl succinate to a shear rate of at least 1/second and an elongational rate of at least 1/second for at least 5 seconds within the crystallization zone, and
   (C) withdrawing the d-alpha-tocopheryl succinate from the crystallization zone at a temperature less than the melting point of the d-alpha-tocopheryl succinate.

5. A process comprising
   (A) introducing an d-alpha-tocopheryl succinate in a fluid state into a crystallization zone at a temperature in the range of about 75° to about 1000° C.,
   (B) subjecting the d-alpha-tocopheryl succinate to a shear rate in the range of 10 to 1000/second and an elongational rate in the range of 1 to 1000/second for at least 20 seconds within the crystallization zone, and
   (C) withdrawing the d-alpha-tocopheryl succinate from the crystallization zone at a temperature less than the melting point of the d-alpha-tocopheryl succinate.

6. A process comprising
   (A) introducing an d-alpha-tocopheryl succinate in a fluid state into a crystallization zone at a temperature in the range of 80° to 90° C.,
   (B) subjecting the d-alpha-tocopheryl succinate to a shear rate in the range of 100 to 600/second and an elongational rate in the range of 100 to 600/second for at least 5 minutes within the crystallization zone, and
   (C) withdrawing the d-alpha-tocopheryl succinate from the crystallization zone at a temperature in the range of 35° to 45° C.

* * * * *